United States Patent
Tanugur Samanci et al.

(10) Patent No.: US 11,564,952 B2
(45) Date of Patent: Jan. 31, 2023

(54) WATER-SOLUBLE AND WATER-INSOLUBLE PROPOLIS PRODUCTS WITH HIGH ANTIOXIDANT CAPACITY AND THEIR PRODUCTION METHODS

(71) Applicant: SBS BILIMSEL BIO ÇÖZÜMLER SANAYI VE TICARET ANONIM SIRKETI, Istanbul (FR)

(72) Inventors: Asli Elif Tanugur Samanci, Istanbul (AR); Taylan Samanci, Istanbul (AR)

( * ) Notice: Subject to any disclaimer, the term of this patent is extended or adjusted under 35 U.S.C. 154(b) by 0 days.

(21) Appl. No.: 16/973,818

(22) PCT Filed: May 5, 2020

(86) PCT No.: PCT/TR2020/050382
§ 371 (c)(1),
(2) Date: Dec. 10, 2020

(87) PCT Pub. No.: WO2020/251489
PCT Pub. Date: Dec. 17, 2020

(65) Prior Publication Data
US 2021/0290693 A1      Sep. 23, 2021

(30) Foreign Application Priority Data
Jun. 13, 2019   (TR) ................. 2019/08777

(51) Int. Cl.
*A61K 35/644*   (2015.01)
*A23L 21/20*   (2016.01)
*A61K 8/18*   (2006.01)

(52) U.S. Cl.
CPC ............ *A61K 35/644* (2013.01); *A23L 21/20* (2016.08); *A61K 8/18* (2013.01)

(58) Field of Classification Search
None
See application file for complete search history.

(56) References Cited

U.S. PATENT DOCUMENTS

| | | | |
|---|---|---|---|
| 5,922,324 A * | 7/1999 | Aga | A61K 31/192 424/539 |
| 2015/0290253 A1* | 10/2015 | Cifter | A61K 36/258 424/537 |
| 2016/0051594 A1* | 2/2016 | Paul | A61K 31/352 435/375 |
| 2017/0209499 A1* | 7/2017 | Suddes | A61K 47/40 |
| 2018/0078584 A1* | 3/2018 | Tang | A61K 8/988 |
| 2020/0085744 A1* | 3/2020 | Gardikis | A61Q 19/00 |

FOREIGN PATENT DOCUMENTS

| | | |
|---|---|---|
| CN | 101978969 A | 2/2011 |
| EP | 101978969 A1 | 9/1998 |
| EP | 2070543 A1 | 6/2009 |
| TR | 2015/04984 | 11/2016 |
| TR | 2016/09851 | 5/2017 |

OTHER PUBLICATIONS

Irigoiti et al. (2021) Trends in Food Science & Technology, 115: 297-306. (Year: 2021).*
Suarez et al. (2022) The Journal of Supercritical Fluids 182: 105538. (Year: 2022).*
International Search Report and Written Opinion of the International Searching Authority for corresponding PCT/FR2020/050382, dated Sep. 9, 2020.

* cited by examiner

*Primary Examiner* — Russell G Fiebig
(74) *Attorney, Agent, or Firm* — Egbert, McDaniel & Swartz, PLLC

(57) ABSTRACT

Disclosed are propolis products suitable for use in various industries such as food, health and cosmetics where propolis, which promote various beneficial biological activities in addition to having antimicrobial, antifungal, antiviral, anti-inflammatory, anti-cancer and anesthetic affects, is extracted correctly to offer it a form suitable for human consumption and with the highest bioavailability, where it is fast and easy to consume. Also disclosed is a method of production thereof.

12 Claims, No Drawings

WATER-SOLUBLE AND WATER-INSOLUBLE PROPOLIS PRODUCTS WITH HIGH ANTIOXIDANT CAPACITY AND THEIR PRODUCTION METHODS

TECHNICAL FIELD

The invention relates to propolis products suitable for use in various industries such as food, health and cosmetics where propolis, which promote various beneficial biological activities in addition to having antimicrobial, antifungal, antiviral, anti-inflammatory, anti-cancer and anesthetic affects, is extracted correctly to offer it to human consumption in a form suitable for human consumption and with highest bioavailability, where it is fast and easy to consume, and methods of production thereof.

PRESENT STATE OF THE ART

Especially since the late 1990s, the discovery of new uses for medicinal and aromatic plants and the increasing demand for natural products have increased the volume of use of these plants every day. Herbal medicinal products have been used for a long time in the treatment or prophylaxis of respiratory diseases. In the treatment or prevention of these diseases, which are mostly caused by viruses, bacteria and/or fungi, the elimination of these harmful organisms as well as the strengthening of the patient's immune system is of great importance.

Propolis is one of the most important bee products. Having many beneficial biological effects such as antibacterial, antifungal, antiviral properties as well as anti-inflammatory, anti-ulcer, local anesthetic, anti-tumor and immunostimulating properties makes its use popular in medicine, apitherapy, diet health and biocosmetics areas. It consists of 150 chemical compounds, more than 20 minerals, wax, resin and polen. In chemical terms, propolis contains highly complex and intense terpenes, benzoic acids, caffeic acids, sinnamic acids and phenolic acids. It has a high flavonoid content.

Propolis is one of the most intense antibiotics found in nature. It is rich in amino acids and trace metals, has very high vitamin content and contains at least 38 valuable bioflavonoids. It is an invaluable antioxidant thanks to its high bioflavonoid content. It has been shown to neutralize at least 21 species of bacteria, 9 species of fungi, 3 protozoa (including giardia) and a wide spectrum of viruses.

Propolis is not suitable for consumption right out of the hive. In order to be converted into a form suitable for human consumption, the contents of the wax and impurities must be removed. Propolis, which has a bioavailability of 2% in its raw form, can reach 100% bioavailability after being fully decomposed in wax and impurities, and our bodies can benefit from propolis, which has been transformed into pure form consisting of antioxidant substances such as phenolic, flavonoid.

The related patent application numbered TR2015/04984 mentions a method for preparing aqueous propolis extract where a step of leaving to rest in a hot water bath at 65° C. is mentioned in order to separate the propolis from the wax which constitute nearly half of the raw propolis in weight. In addition, during the extraction process, first acid, then base are added to the medium.

In the related patent application numbered TR2016/09851, the final product formed by the method of extraction of propolis with vegetable oil is intended to be suitable for use on the skin in cosmetic and pharmaceutical fields. A single step extraction process with oil is applied. It was also heated to 50° C. degrees.

The solutions offered in the prior art are inadequate. Temperature exposure of propolis extract which is a natural product, acid-base addition leads to degradation of propolis. Furthermore, it is not possible to extract high bio-availability propolis with a single step extraction process.

Raw propolis is required to be extracted correctly due to impurities in its contents and undigested components such as wax, and to be offered for consumption with the highest bio-availability, which preserves the highest number of useful components in its contents.

Today, analyses of commercially available propolis-containing products show that the propolis content information written on the labels is incorrect or extraction methods are insufficient. Raw propolis is required to be extracted correctly due to impurities in its contents and undigested components such as wax, and to be offered for consumption with the highest bio-availability, which preserves the highest amount of useful components in its contents. The antioxidant content and bioavailability of the products on the market are very low. With current techniques, propolis, which is not extracted correctly, is a product far from serving its purpose for consumption due to very low beneficial component content.

Therefore, due to the disadvantages described above and due to the lack of existing solutions on the subject, a development in the relevant technical field is required.

BRIEF DESCRIPTION OF THE INVENTION

The present invention relates to propolis products and production methods thereof that meets the requirements mentioned above, while eliminating all disadvantages and providing some additional advantages.

The primary purpose of the invention is to provide a method of obtaining a correctly extracted, high bioavailability propolis extract.

Another purpose of the invention is to provide the steps applied during the method in such a way as to give an appropriate and efficient result that does not impair the stability of the propolis product.

A purpose of the invention is to obtain propolis extract with high flavonoid content which is extracted correctly and which cause various beneficial biological activities to take place in addition to having antioxidant, antimicrobial, antifungal, anti-inflammatory, anti-cancer and effects.

A purpose of the invention is to provide raw materials or final products to be used for health diet, apitherapy, biocosmetic purposes in the food, health and cosmetics industries in liquid or solid form of the obtained propolis extract.

In order to achieve the aforementioned purposes, the invention comprises a method to obtain propolis product with high antioxidant capacity, comprising the process steps of;
- crumbling raw propolis by passing through the grinder,
- mixing the crumbled propolis with a solvent material selected from the group consisting of ethyl alcohol, propylen glycol, glycerol, mixture of ultrapure water: mineral water, olive oil, almond oil, linseed oil, fish oil, pomegranate juice, orange juice, beetroot juice, grape juice,
- mixing the obtained solution by adding lemon juice or apple cider vinegar as acid regulator,
- shaking the obtained solution,
- degassing the shaken solution, centrifuging the degassed solution, analysing phenolic flavonoid matter in extract obtained after centrifuge, determination of dry matter in the extract obtained after centrifuge, obtaining the desired final products from the extracts with suitable analysis results.

The invention also comprises the use of propolis products obtained with the aforementioned method and the use of these products for diet health, apitherapy and biocosmetic purposes in the food, health and cosmetic industries.

The structural and characteristic features and all advantages of the invention will be understood more clearly through the detailed explanation and therefore assessment should be made by considering the detailed explanation.

DETAILED DESCRIPTION OF THE INVENTION

In this detailed description, propolis products and production methods of the invention are described only for a better understanding of the subject matter, without posing any limitations.

The invention relates to propolis products suitable for use in various industries such as food, health and cosmetics where propolis, which promote various beneficial biological activities in addition to having antimicrobial, antifungal, antiviral, anti-inflammatory, anti-cancer and anesthetic affects, is extracted correctly to offer it to human consumption in a form suitable for human consumption and with highest bioavailability, where it is fast and easy to consume, and a method of production thereof.

Raw propolis must be extracted with a solvent and removed from impurities because it cannot be digested directly due to impurities in its contents and non-digestible components such as wax. Table 1 gives solvent substances that can be used in the method of the invention.

TABLE 1

Raw materials used in the method of the invention

| Solvents that can be used | Preferred quantities for each 300 gr raw propolis extraction (gr) | Usable quantities for each 200-500 gr raw propolis extraction (gr) |
|---|---|---|
| Ethyl alcohol | 1000 | 750-1500 |
| Propolis | 300 | 200-500 |
| Propylene glycol | 100 | 80-100 |
| Glycerol | 100 | 80-100 |
| Ultra pure water | 275 | 250-300 |
| Olive oil | 1000 | 750-1500 |
| Almond oil | 1000 | 750-1500 |
| Linseed oil | 1000 | 750-1500 |
| Fish oil | 1000 | 750-1500 |
| Orange juice | 1000 | 750-1500 |
| Pomegranate juice | 1000 | 750-1500 |
| Grape juice | 1000 | 750-1500 |
| Beet juice | 1000 | 750-1500 |
| Mineral water | 500 | 250-1000 |
| Acid regulators that can be used | | |
| Lemon juice | 100 | 50-200 |
| Apple cider vinegar | 100 | 50-200 |

Raw Propolis: Propolis is an herbal substance in the form of sticky resin collected by bees from trees and plants and transported to hives. It is a bee product that has the property of being a natural antibiotic. Propolis, which has natural antibiotic properties, possesses antioxidant, antimicrobial, antifungal, antivirus, anti-inflammatory, anticancer and anaesthetic effects as well as many beneficial biological activities. It enhances the immune system. It is known to be effective against cancer, inflammatory diseases, virus and bacterial diseases.

Solvent: Raw propolis should not be consumed directly due to impurities in its contents and non-digestible components such as wax, and should be extracted and removed from impurities. Solvent is the agent that allows dissolution of raw propolis and the transport of active substances. In the method of the invention for obtaining a propolis extract with high flavonoid content, ethanol (ethanol) with over 90% purity suitable for use in foods, propylene glycol, ultra pure water and mineral water mixture in the ratio of 1:1-1.3, olive oil, almond oil, linseed oil, fish oil or similar oils, pomegranate juice, orange juice, beet juice, grape juice or similar juices suitable for use in foods or different solvents depending on the final product and compositions desired to be obtained and not harmful to human health can be used as solvent. Furthermore, although high levels of extract can be obtained using solvents such as acetone, methanol, ethyl acetate, chloroform, hexane, these are not preferred solvents since they are not suitable for human health.

Ethanol, ethyl alcohol or vegetable alcohol; is a colorless chemical compound derived from plants. Today it is used as solvent in vitamin syrups.

Ultra Pure Water is the more purified state of pure water. Pure water is water in which the mineral substances in the water are separated. Ultra pure water is water with a conductivity value of 0.055 µS/cm (25° C.) or electrical resistance of 18.2 Megaohm-cm.

Propylene glycol is a petroleum oil kind of compound with many uses in the commercial industry. It is odorless and has no specific taste. Propylene glycol is used in the food, cosmetic, pharmaceutical and plastic industries.

Olive oil is a type of vegetable oil and is very rich in vitamins E and K. Furthermore, it contains calcium, iron, sodium and potassium. It particularly nourishes and protects the skin.

Almond oil, a type of vegetable oil, is very beneficial in terms of hair and especially skin health. The fact that almond oil contains high amounts of vitamin A and K makes it important for health. In addition, it contains a significant amount of protein.

Linseed oil is a type of vegetable oil that protects heart health thanks to its alpha linolenic acid content and reduces the risk of developing heart disease. It reduces the risk of a heart attack. It contains omega 3 and omega 6 fatty acids.

Fish oil is a type of animal fat that lowers high cholesterol levels. It protects blood vessels and reduces the risk of heart attack and stroke due to balancing of cholesterol. It contains high levels of Omega 3.

Orange juice can reduce blood pressure as well as "bad" cholesterol levels, preventing cardiovascular problems as a result. It is a very rich source of vitamin C, which is ideal for preventing colds. It also helps regulating the bowel system.

Pomegranate juice regulates cholesterol and blood sugar and prevents it from increasing. It regulates blood pressure. It protects cardiovascular health and regulates its function. Protects and increases body's resistance to infection. It provides toxin excretion due to its diuretic effect. Promotes smooth skin appearance.

Grape juice reduces the risk of blood clots. It reduces low-density lipoprotein (LDL), in other words, bad cholesterol. It prevents damage to blood vessels in the heart. It helps maintain a healthy blood pressure level. It has an anti-aging effect on the skin due to the acid regulators it contains.

Beet juice contains vitamin A, vitamin C, vitamin B6, vitamin B1, vitamin B2, acid regulators, sodium, calcium, sulfur, chlorine, copper, iodine, natural sugar, bioflavonoids, and potassium. It is also a good source of dietary fiber, carbohydrates, niacin, folic acid, biotin and magnesium.

Acid regulator: In the method of the invention for obtaining propolis extract with high flavonoid content, it is used for increasing the acidity of the solution consisting of propolis and solvent. When vegetable oils, animal fats or a mixture of 1:1-1:3 ultra pure water and mineral water or ethanol is used as solvent; lemon juice can be used as the acid regulator. When propylene glycol or aforementioned fruit juices are used as solvent; apple cider vinegar can be used as the acid regulator. In addition, different acid regulators may be preferred for different solvents.

In the production method of the invention for producing propolis products, the raw propolis specified in Table 1 is passed through the grinder and crumbled. The crumbled propolis is mixed with the selected solvent at room temperature, again in quantities specified in Table 1. As a solvent, a solvent selected from Table 1 can be used in specified quantities. Ethyl alcohol and propylene glycol are suitable for use in food; and no solvent is subjected to heating process.

Acid regulators with amounts specified in Table 1 are added to the obtained solution at room temperature and mixed. When using the aforementioned oils or a mixture of ultra pure water and mineral water or ethanol as a solvent, lemon juice may be used in the amounts given in Table 1 as an acid regulator. When propylene glycol or aforementioned fruit juices are used as solvent; apple cider vinegar can be used as the acid regulator in the amounts given in Table 1.

The aforementioned solution containing propolis and solvent and acid regulators is constantly shaken in the dark for at least 7 days at a 20-30° C. temperature environment. At the end of this period, said solution is subjected to degassing process in ultrasonic bath at 25° C. for 3 hours. During the degassing process, caution has been taken not to exceed 30° C. temperature. The solution, which is freed from the gases in it by degassing process, is centrifuged at 10 000 g for a period of 20-30 minutes.

A sample is taken from the upper phase obtained by the centrifuge process and the bioavailable fenolic flavonoid material content of the propolis is analysed using LC-MMS (Liquid Cromotography-Mass/Mass Spectrometer). The condition of having more than 10 mg/g of galangin, pinocembrin, crystalline, cinnamic acid and having more than 5 mg/g of p-coumaric acid, ferulic acid, caffeic acid phenethyl ester (CAPE) is required in the analysis results. If the result of the analysis is above the desired values, dry matter determination of the sample is applied.

When the results of the analysis are not appropriate, the mentioned solution is again constantly shaken in the dark for at least 7 days in a 20-30° C. temperature environment; degassed in ultrasonic bath at 25° C. for 3 hours; and centrifuged at 10 000 g for a period of 20-30 minutes. A new sample is taken from the upper phase resulting from the centrifuge process and in LC-MMS, the phenolic flavonoid substance content is analyzed. The condition of having more than 10 mg/g of galangin, pinocembrin, crystalline, cinnamic acid and having more than 5 mg/g of p-coumaric acid, ferulic acid, caffeic acid phenethyl ester is required in the analysis results. If the result of the analysis is above the desired values, dry matter determination of the sample is applied.

In dry matter determination, the amount of dry matter should be 20% to 30% for products containing ethyl alcohol and 10% to 15% for products containing propylene glycol or glycerol. In products where oil and juice are as solvent, first the amount of dry matter of the solvent then the amount of dry matter of the propolis extract in the relevant solvent is calculated and the final products should be obtained so that the difference of the dry matter is 5% to 15%. In addition, calculation is made by taking into account the percentage of propolis present in the final product. For example, the product is prepared based on an antioxidant capacity of 100 mg trolox equivalent/ml sample in the product containing 10% propolis, and if the product is to contain 20% propolis, 100*2 mg trolox equivalent/ml sample is required.

In the obtained solution mentioned above, if the amount of dry matter has reached the desired rate, the final product is obtained by going through the filling and packaging processes. However, in the mentioned solution, if the amount of dry matter has not reached the desired rate, the extract is subjected to freeze-drying process. By means of this method, the amount of bound water in the extract is removed under vacuum and the amount of dry matter is increased. After the freeze-drying process, a new sample is taken from the extract and dry matter is determined. If the result of the analysis is above the desired values, the extracts are added to liquid foods such as water, milk, fruit juice and can be dissolved in liquid form; in extracts with suitable analysis results, products in solid form in powder state is obtained by freeze-drying. The final products are filled and packaged appropriately in order to be used in food, health and cosmetics industries; for diet health, apitherapy, biochemistry purposes.

With the method described above, products with high bioavailability, suitable for human consumption, in different forms and modes of consumption can be produced by preserving the beneficial components in propolis.

Propolis products with high flavonoid content, can be consumed by infants, children and adults starting at 6 months of age, since they are natural and healthy. Propolis has no known side effects. Liquid drip products containing propolis extract containing propylene glycol can be used by 6-month babies starting with 1 drop per day and increasing by 1 drop per month, 5 drops per day between 1-2 years of age, 10 drops per day between 2-7 years of age, 15 drops per day between 7-13 years of age, 20 drops per day at 13 and older ages. During the periods of illness when the body is immunocompromised, the dosage can be doubled to 2 times. Extracts of propolis dissolved in ethanol can be used by dripping onto popular products such as honey, yogurt, molasses. Propolis extracts dissolved in proplylene glycol can be consumed by dripping into liquid foods such as water, juice, milk, tea, coffee. Propolis extracts dissolved in vegetable oils or animal fat can be consumed by adding to salads and meals, or can be used by applying to the skin surface or by adding to various cosmetic products. Propolis extracts dissolved in fruit juice can be mixed in water or yoghurt and consumed between 30-50 drops by adults and 10-20 drops by children, depending on the percentage of propolis content.

The invention claimed is:
1. A method for producing a propolis product comprising:
 (a) grinding raw propolis into crumbles with a grinder;
 (b) mixing the crumbles with solvent material, wherein the solvent material is selected from the group consist- ing of: ethyl alcohol, propylene glycol, glycerol, a mixture of ultra-pure water and mineral water, olive oil, almond oil, linseed oil, fish oil, pomegranate juice, orange juice, beetroot juice, grape juices and mixtures thereof;
(c) adding an acid regulator to the mixed crumbles and solvent material to produce an obtained solution, wherein the acid regulator is selected from the group consisting of: lemon juice, apple cider vinegar and mixtures thereof;
(d) shaking the obtained solution in a dark environment for at least one week after the acid regulator is added;
(e) degassing the shaken obtained solution;
(f) centrifuging the degassed solution to produce a supernatant extract of the degassed solution;
(g) analyzing phenolic flavonoid matter of the supernatant extract;
(h) determining dry matter in the extract;
(i) processing the extract to produce the propolis product.

2. The method of claim 1, wherein the step of mixing comprises:
mixing 200 to 500 grams of the crumbles with 750 to 1500 grams of the solvent material, the solvent material selected from the group consisting of ethyl alcohol, olive oil, almond oil, linseed oil, fish oil, pomegranate juice, orange juice, beetroot juice, and grape juice.

3. The method of claim 1, wherein the step of mixing comprises:
mixing 200 to 500 grams of the crumbles with 800 to 100 grams of the solvent material, the solvent material selected from the group consisting of propylene glycol and glycerol.

4. The method of claim 1, wherein the step of mixing comprises:
mixing 200 to 500 grams of the crumbles with 250 to 300 grams of the ultra-pure water and 250 to 1000 grams of mineral water in the weight ratio of 1:1 to 1:3 of the crumbles with the ultra-pure water and the mineral water.

5. The method of claim 1, wherein the step of mixing comprises:
mixing 200 to 500 grams of the crumbles with 250 to 300 grams of the ultra-pure water and 250 to 1000 grams of mineral water in the weight ratio of 1:1 to 1:3 of the crumbles with the ultra-pure water and the mineral water.

6. The method of claim 1, wherein the step of adding the acid regulator comprises:
mixing 50 to 200 grams of the acid regulator to 200-500 grams of the crumbles.

7. The method of claim 1, wherein the step of degassing comprises:
degassing the shaken obtained, solution in an ultrasonic bath for three hours at 25° C.

8. The method of claim 1, wherein the step of centrifuging comprises:
centrifuging the degassed solution at 10,000 G for twenty minutes.

9. The method of claim 1, wherein the step of analyzing comprises:
analyzing the phenolic flavonoid matter using LC-MMS, W if a flavonoid material content is at least 10 mg/g of p-coumaric acid, ferulic acid, caffeic acid phenethyl ester value, the process step determining dry matter occurs.

10. The method of claim 1, wherein the step of analyzing comprises:
determining if an amount of dry matter is 20 to 30% by weight for product containing ethyl alcohol as solvent and if the amount of the dry matter is 10 to 15% by weight for product containing propylene glycol or glycerol as the solvent and if the extract of the solvent and the dry matter has a difference of 5 to 15% by weight for product containing at least one of the olive oil, the almond oil, the linseed oil, the fish oil, the pomegranate juice, the orange juice, the beetroot juice, and the grape juice, the step of producing the final product occurs.

11. The method of claim 1, wherein the step of processing the final product comprises:
adding the extract to a liquid food.

12. The method of claim 1, wherein the step of processing the final product comprises:
freeze-drying the extract in powder form.

* * * * *